United States Patent
Yoshida et al.

(10) Patent No.: US 9,051,234 B2
(45) Date of Patent: *Jun. 9, 2015

(54) METHOD FOR PRODUCING ALKANEDIOL

(71) Applicant: UBE INDUSTRIES, LTD., Ube-shi (JP)

(72) Inventors: Yasutaka Yoshida, Ube (JP); Kenji Hirotsu, Ube (JP); Takashi Doi, Ube (JP); Kouichi Kashiwagi, Ube (JP); Ryo Fujimoto, Ube (JP); Ryousuke Katsura, Ube (JP); Satoru Fujitsu, Ube (JP)

(73) Assignee: UBE INDUSTRIES, LTD., Ube-shi (JP)

( * ) Notice: Subject to any disclaimer, the term of this patent is extended or adjusted under 35 U.S.C. 154(b) by 0 days.

This patent is subject to a terminal disclaimer.

(21) Appl. No.: 14/357,107

(22) PCT Filed: Nov. 19, 2012

(86) PCT No.: PCT/JP2012/079998
§ 371 (c)(1),
(2) Date: May 8, 2014

(87) PCT Pub. No.: WO2013/073704
PCT Pub. Date: May 23, 2013

(65) Prior Publication Data
US 2014/0316167 A1    Oct. 23, 2014

(30) Foreign Application Priority Data
Nov. 18, 2011    (JP) .................................. 2011-252341

(51) Int. Cl.
| | |
|---|---|
| *C07C 29/80* | (2006.01) |
| *C07C 29/132* | (2006.01) |
| *B01J 23/80* | (2006.01) |
| *B01J 23/889* | (2006.01) |
| *B01J 23/83* | (2006.01) |
| *C07C 29/84* | (2006.01) |
| *B01J 23/78* | (2006.01) |
| *C07C 29/154* | (2006.01) |

(52) U.S. Cl.
CPC ................ *C07C 29/132* (2013.01); *B01J 23/80* (2013.01); *B01J 23/8892* (2013.01); *B01J 23/83* (2013.01); *C07C 29/84* (2013.01); *B01J 23/78* (2013.01); *C07C 29/154* (2013.01)

(58) Field of Classification Search
USPC .......................................... 568/865, 866, 867
See application file for complete search history.

(56) References Cited

U.S. PATENT DOCUMENTS

| | | | |
|---|---|---|---|
| 627,293 | A | 6/1899 | Brighton |
| 2,768,978 | A | 10/1956 | Robertson |
| 5,302,569 | A | 4/1994 | Horn et al. |
| 5,478,789 | A | 12/1995 | Hattori et al. |
| 2003/0187309 | A1 | 10/2003 | Prinz et al. |

FOREIGN PATENT DOCUMENTS

| | | |
|---|---|---|
| CN | 1108585 A | 9/1995 |
| DE | 918325 | 9/1954 |
| JP | 62 39535 | 2/1987 |
| JP | 6 63406 | 3/1994 |
| JP | 6 170231 | 6/1994 |
| JP | 6 345674 | 12/1994 |
| JP | 7 100381 | 4/1995 |
| JP | 2001 316311 | 11/2001 |
| JP | 2003 277306 | 10/2003 |
| JP | 2005 35974 | 2/2005 |
| JP | 2009 46417 | 3/2009 |

OTHER PUBLICATIONS

Organic Synthesis Coll. vol. 3, p. 693 (1955); vol. 26 p. 83 (1946).
International Search Report Issued Feb. 12, 2013 in PCT/JP12/079998 Filed Nov. 19, 2012.
Combined Chinese Office Action and Search Report issued Jan. 20, 2015 in Patent Application No. 201280053721.8 (with English translation of categories of cited documents).

*Primary Examiner* — Sikarl Witherspoon
(74) *Attorney, Agent, or Firm* — Oblon, McClelland, Maier & Neustadt, L.L.P.

(57) ABSTRACT

Provided by the present invention is a method for producing an alkanediol, such as 1,5-pentanediol, with a high reaction selectivity thereto by reacting a cyclic ether group-containing methanol such as tetrahydrofurfuryl alcohol by using a non-chromium catalyst not containing chromium atom. More specifically, the method is to produce an alkanediol having hydroxy groups at both molecular terminals shown by the formula (2), includes reacting a cyclic ether group-containing methanol shown by the formula (1) with hydrogen in the presence of a metal catalyst which contains copper atom, at least one co-existing atom selected from the group consisting of elements of the third to the sixth periods of the II to XIV groups (excluding chromium) in the periodical table and lanthanide elements.

9 Claims, No Drawings

METHOD FOR PRODUCING ALKANEDIOL

TECHNICAL FIELD

The present invention relates to a method for producing an alkanediol by convenient procedures with an industrially low cost, a high reaction selectivity, and a superior productivity by using a methanol having a cyclic ether group as a manufacturing raw material thereof.

For example, tetrahydrofurfuryl alcohol used in the present invention is one of the so-called biomass raw materials; and 1,5-pentanediol produced by using these as a manufacturing raw material thereof is useful as a raw material (monomer) for polymers such as a polyester, a polycarbonate, and a polyurethane, and as a raw material for a pharmaceutical drug and an agricultural chemical, an additive for a resin, a solvent, and the like.

BACKGROUND ART

In the past, to produce an alkylene polyol, such as 1,5-pentanediol, by using a methanol having a cyclic ether group (hereinafter, this is sometimes referred to as "cyclic ether group-containing methanol"), such as tetrahydrofurfuryl alcohol, as a manufacturing raw material thereof, a method has been widely known in that a methanol having a furan ring or a pyran ring as the cyclic ether group is decomposed by hydrogenation in the presence of a metal catalyst (see, for example, Patent Documents 1 to 3).

For example, in Patent Document 1 and Non-Patent Document 1, a method is reported in that 1,5-pentanediol is produced from tetrahydrofurfuryl alcohol in the presence of a copper-chromium type catalyst; and in Patent Document 2, a method is reported in that tetrahydrofurfuryl alcohol is produced from furfural in the presence of a cobalt-aluminum type catalyst or a copper-aluminum type catalyst, and in addition, 1,2-pentanediol and 1,5-pentanediol are produced from furfural by using a copper-aluminum type catalyst (Example 4).

On the other hand, a method for producing an alkylene polyol by using a metal catalyst other than a copper type catalyst has been reported in recent years; and for example, in Patent Document 3, a ring opening method of a cyclic ether was reported in that the reaction selectivity to a certain bond of a cyclic ether group in the ring opening is high by using a metal catalyst containing rhodium and one or more metal atom selected from rhenium, molybdenum, and tungsten supported on a carrier. In this ring opening method, a method for producing 1,5-pentanediol or 1,6-hexanediol from tetrahydrofurfuryl alcohol or tetrahydropyran-2-methanol respectively in the presence of the afore-mentioned catalyst is disclosed.

Patent Document 1: U.S. Pat. No. 2,768,978
Patent Document 2: U.S. Pat. No. 627,293
Patent Document 3: Japanese Patent Laid-Open Publication No. 2009-46417
Non-Patent Document 1: Organic Syntheses Coll. Vol. 3, p. 693 (1955); Vol. 26, p. 83 (1946).

SUMMARY OF THE INVENTION

Problems to be Solved by the Invention

However, for example, in the method described in Patent Document 1, a good reaction condition to give the reaction selectivity to the by-product pentanol of 6% or less could not be found also as an industrial method; and in the method described in Non-Patent Document 1, the yield of 1,5-pentanediol was described, but the reaction selectivity thereto was not specifically mentioned.

Similarly, in the method of Patent Document 2, the reaction selectivity of 30% was reported as a mixture of 1,5-pentanediol and 1,2-pentanediol, while the selectivity to 1,5-pentanediol was not mentioned. Accordingly, any of them has not been fully satisfactory as the industrial manufacturing methods.

Moreover, the biggest problem in Patent Document 1 and Non-Patent Document 1 is that these methods use a catalyst that contains a harmful chromium atom. It is widely known that this chromium shows a strong harmful effect on a human body even with a minute amount, thereby requiring very complicated procedures to remove chromium completely; and thus, these methods are not industrially practicable. Accordingly, in recent years, there is a tendency to avoid use of the catalyst that contains chromium atom (see, for example, the paragraph (0004) in Japanese Patent Laid-Open Publication No. H06-345674).

On the other hand, in the method of Patent Document 3, it is disclosed that to satisfactorily achieve both the reaction conversion and the reaction selectivity is difficult when the reaction is carried out in a solution not containing water; and thus, it is described therein that a solution such as an aqueous solution containing 5% of tetrahydrofurfuryl alcohol is used as the manufacturing raw material. However, for example, use of the low concentration aqueous solution in which only 5% of tetrahydrofurfuryl alcohol is contained as the raw material cannot be regarded as economical because of low production efficiency; and moreover, the process to separate water-soluble 1,5-pentanediol from water after completion of the reaction is complicated, and thus, this method cannot be considered to be a suitable industrial method either.

Accordingly, the present invention has an object to provide a method for producing an alkanediol, such as 1,5-pentanediol, with a high reaction selectivity thereto by reacting a cyclic ether group-containing methanol, such as tetrahydrofurfuryl alcohol, by using a non-chromium catalyst free from chromium atom.

Means for Solving the Problems

That is, the present invention relates to the following (1) to (16).

(1) A method for producing an alkanediol having hydroxy groups at both molecular terminals shown by the following formula (2), comprising reacting a cyclic ether group-containing methanol shown by the following formula (1) with hydrogen in the presence of a metal catalyst which contains copper atom and at least one co-existing atom selected from the group consisting of elements of the third to the sixth periods of the II to XIV groups (excluding chromium) in the periodical table and lanthanide elements,

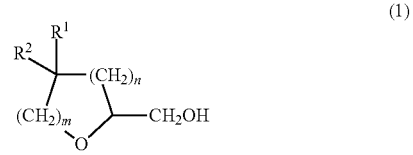

(1)

wherein $R^1$ and $R^2$ represent a hydrogen atom, a fluorine atom, a methyl group, or an ethyl group, and these may be the same or different with each other; "n" and "m" represent number of a methylene group; "n" represents an integer of 0, 1, or 2; "m" represents an integer of 1 or 2; "n" and "m" may be the same or different with each other, and "n+m" is 2 to 4,

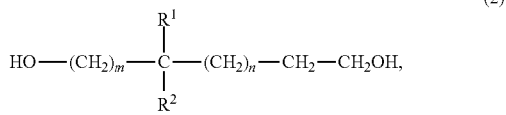
(2)

wherein $R^1$ and $R^2$ as well as "n" and "m" represent the same as those of the formula (1).

(2) The method for producing an alkanediol according to (1), wherein the co-existing atom comprises at least one atom "B" selected from the group consisting of zinc, iron, aluminum, and silicon.

(3) The method for producing an alkanediol according to (2), wherein the atom "B" is zinc atom.

(4) The method for producing an alkanediol according to (2) or (3), wherein mass ratio of the copper atom to the atom "B" (copper atom/atom "B") is in the range of 10/90 to 99/1.

(5) The method for producing an alkanediol according to any one of (2) to (4), wherein the co-existing atom further comprises, in addition to the atom "B", at least one atom "C" selected from the group consisting of barium, calcium, manganese, lanthanum, cerium, and magnesium.

(6) The method for producing an alkanediol according to (5), wherein as to the content of the atom "C", mass ratio of the copper atom and the atom "B" to the atom "C" (sum of copper atom and atom "B"/atom "C") is in the range of 10/90 to 99/1.

(7) The method for producing an alkanediol according to any one of (1) to (6), wherein use amount of the metal catalyst relative to the cyclic ether group-containing methanol is in the range of 0.03 to 10% by mass.

(8) The method for producing an alkanediol according to any one of (1) to (7), wherein the cyclic ether group-containing methanol is tetrahydrofurfuryl alcohol and the alkanediol is 1,5-pentanediol.

(9) The method for producing an alkanediol according to (8), wherein the said tetrahydrofurfuryl alcohol is tetrahydrofurfuryl alcohol synthesized by using furfural as a raw material thereof.

(10) A metal catalyst for hydrogenation reaction, obtainable by using a catalyst precursor mainly comprising carbonate salts which includes copper, zinc, and at least one atom selected from the group consisting of barium, calcium, manganese, lanthanum, zirconium, and cerium.

(11) A metal catalyst obtainable by using a catalyst precursor mainly comprising carbonate salts which includes copper, zinc and at least one atom selected from the group consisting of calcium, lanthanum, and manganese.

(12) A metal catalyst obtainable by using a catalyst precursor mainly comprising carbonate salts which includes copper, zinc and at least one atom selected from the group consisting of zirconium and cerium.

(13) A metal catalyst obtainable by using a catalyst precursor mainly comprising carbonate salts which includes copper, zinc, barium, and manganese or lanthanum.

(14) A metal catalyst obtainable by using a catalyst precursor mainly comprising carbonate salts which includes copper, zinc, barium, manganese, and lanthanum.

(15) A metal catalyst obtainable by using a catalyst precursor mainly comprising carbonate salts which includes copper, zinc, and barium.

(16) Use of a metal catalyst obtainable by using a catalyst precursor mainly comprising carbonate salts which includes copper, zinc and at least one atom selected from the group consisting of barium, calcium, manganese, lanthanum, zirconium, and cerium for a reaction using hydrogen.

According to the present invention, provided is a method for producing an alkanediol, such as 1,5-pentanediol, with a high reaction selectivity thereto by reacting a cyclic ether group-containing methanol such as tetrahydrofurfuryl alcohol by using a certain non-chromium catalyst.

Especially, the present invention also involves discovery of a production method found, wherein the method uses a certain non-chromium copper-containing metal catalyst as the reaction catalyst capable of ring-opening of an ether ring at a certain bond with a high regioselectivity in a hydrogenolysis reaction of tetrahydrofurfuryl alcohol as a manufacturing raw material.

Therefore, according to the present invention, provided is a method for producing 1,5-pentanediol with a high reaction selectivity thereto while suppressing production of various by-products including alkanediols having a secondary hydroxy group, such as 1,2-pentanediol, and alkyl alcohols, such as 1-pentanol, these having been by-produced in conventional production methods. Especially, discovery was made as to a non-chromium copper-containing catalyst being able to suppress to the lowest degree by-production of a branched alkanediol having a secondary hydroxy group, such as 1,2-pentanediol, which is difficult to be separated from 1,5-pentanediol; and based on this discovery, the present invention could be established. It is reported that for example, a branched or a cyclic alkanediol having a secondary hydroxy group such as 1,2-pentanediol which is contained as impurities in 1,5-pentanediol has a bad influence to manufacturing of a polyurethane (see, the paragraph (0005) of Japanese Patent Laid-Open Publication No. 2001-316311). Therefore, the present invention provides an alkanediol containing less amount of impurities thereby suitable, for example, as a manufacturing raw material of a polyurethane resin.

MODES FOR CARRYING OUT THE INVENTION

The method for producing an alkanediol of the present invention is achieved by reacting hydrogen with a cyclic ether group-containing methanol, such as tetrahydrofurfuryl alcohol, in the presence of a metal catalyst which contains copper atom and at least one co-existing atom (atom "B" and/or atom "C") selected from the group consisting of the elements of the third to the sixth periods of the II to XIV groups (excluding chromium) in the periodical table. In the present invention, an alkanediol shown by the afore-mentioned formula (2), such as 1,5-pentanediol, can be obtained with a high selectivity thereto by selecting a certain metal catalyst like this.

Raw material: cyclic ether group-containing methanol shown by the formula (1)

In the production method of the present invention, the cyclic ether group-containing methanol used as the raw material is shown by the following formula (1).

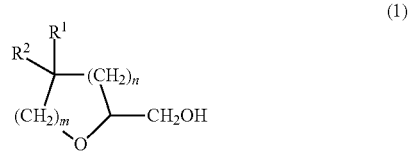
(1)

In the formula (1), $R^1$ and $R^2$ represent a hydrogen atom, a fluorine atom, a methyl group, or an ethyl group, and these may be the same or different with each other; "n" and "m" represent number of a methylene group; "n" represents an integer of 0, 1, or 2; "m" represents an integer of 1 or 2; "n" and "m" may be the same or different with each other; and "n+m" is 2 to 4.

It is preferable that the cyclic ether group-containing methanol have 5 to 7 carbon atoms as a total.

Accordingly, example of the cyclic ether group-containing methanol shown by the general formula (1) includes the compounds shown by the following general formulae (1a) to (1e).

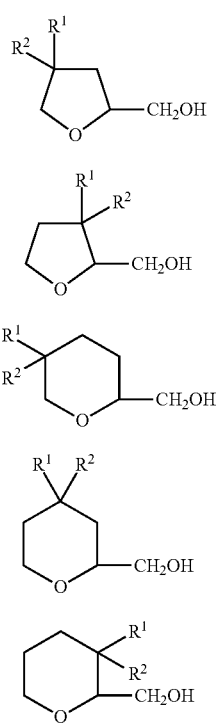

(In the formulae (1a) to (1e), $R^1$ and $R^2$ represent the same meanings as those of the formula (1)).

More specific example of the cyclic ether group-containing methanol shown by the general formula (1) to be used includes; preferably tetrahydrofurfuryl alcohol, 3-methyltetrahydrofurfuryl alcohol, 3,3-dimethyltetrahydrofurfuryl alcohol, 3-fluorotetrahydrofurfuryl alcohol, 3,3-difluorotetrahydrofurfuryl alcohol, 4-methyltetrahydrofurfuryl alcohol, 4,4-dimethyltetrahydrofurfuryl alcohol, 4-fluorotetrahydrofurfuryl alcohol, 4,4-difluorotetrahydrofurfuryl alcohol, tetrahydropyran-2-methanol, 4-methyltetrahydropyran-2-methanol, 5-methyltetrahydropyran-2-methanol, 3,3-dimethyltetrahydropyran-2-methanol, 4,4-dimethyltetrahydropyran-2-methanol, 5,5-dimethyltetrahydropyran-2-methanol, 3-fluorotetrahydropyran-2-methanol, 4-fluorotetrahydropyran-2-methanol, 5-fluorotetrahydropyran-2-methanol, 3,3-difluorotetrahydropyran-2-methanol, 4,4-difluorotetrahydropyran-2-methanol, and 5,5-difluorotetrahydropyran-2-methanol; more preferably tetrahydrofurfuryl alcohol, 4-methyltetrahydrofurfuryl alcohol, 4,4-dimethyltetrahydrofurfuryl alcohol, 4-fluorotetrahydrofurfuryl alcohol, 4,4-difluorotetrahydrofurfuryl alcohol, and tetrahydropyran-2-methanol; still more preferably tetrahydrofurfuryl alcohol and tetrahydropyran-2-methanol; and further still more preferably tetrahydrofurfuryl alcohol.

Tetrahydrofurfuryl Alcohol:

As to tetrahydrofurfuryl alcohol used most preferably in the manufacturing method of the present invention, a commercially available compound thereof may be used as it is, or after it is further purified; and thus, any of them may be used. For example, it is known that tetrahydrofurfuryl alcohol may be produced from a non-edible biomass such as non-edible corncob (corn core). Therefore, to use tetrahydrofurfuryl alcohol derived from the biomass like this is preferable in view of the green chemistry.

Product: Alkanediol Shown by the Formula (2)

The alkanediol obtained by the reaction of the present invention may be shown specifically by the following general formula (2).

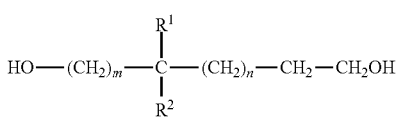

In the general formula (2), $R^1$ and $R^2$ represent, the same as the formula (1), specifically a hydrogen atom, a fluorine atom, a methyl group, or an ethyl group, and these may be the same or different with each other; "n" and "m" represent number of a methylene group; "n" represents an integer of 0, 1, or 2; "m" represents an integer of 1 or 2; "n" and "m" may be the same or different with each other; "n+m" is 2 to 4.

In the production method of present invention, an objective alkanediol can be obtained with a high reaction selectivity thereto especially when the manufacturing raw material thereof is a cyclic ether group-containing methanol, such as tetrahydrofurfuryl alcohol, shown by the general formula (1a) or (1b).

Metal Catalyst

The metal catalyst used in the present invention contains copper atom and at least one co-existing atom selected from the group consisting of the elements of the third to the sixth periods of the II to XIV groups (excluding chromium) in the periodical table and lanthanide elements. This co-existing atom includes at least one metal atom selected from the group consisting of the atoms "B" and the atoms "C" shown below. Here, the co-existing atoms mean the atoms to constitute the metal catalyst together with copper atom contained in the metal catalyst.

The metal catalyst used in the present invention includes a supported metal catalyst in which copper atom and co-existing atoms are supported on a later-mentioned carrier. Moreover, in the reaction of the present invention, the metal catalyst may be used solely or as a mixture of two or more kinds of it.

In the metal catalyst used in the reaction of present invention, mass ratio of the copper atom to the co-existing atom (copper atom/co-existing atom) is not particularly limited; however, usually in the range of 0.1/99.9 to 99.9/0.1, preferably in the range of 1/99 to 99/1, or more preferably in the range of 5/95 to 95/5, in order to enhance the reaction selectivity to the alkanediol having the hydroxy groups at the both molecular terminals thereof. Here, the said mass ratio is the content ratio of the metal atoms in the metal catalyst.

Next, the co-existing atoms, the atom "B" and the atom "C", will be explained. Atom "B":

As to the co-existing atom "B" of the present invention, used is at least one metal atom selected from the group consisting of magnesium (Mg), calcium (Ca), barium (Ba), lanthanum (La), cerium (Ce), titanium (Ti), zirconium (Zr), vanadium (V), niobium (Nb), molybdenum (Mo), tungsten (W), manganese (Mn), rhenium (Re), iron (Fe), cobalt (Co), osmium (Os), zinc (Zn), aluminum (Al), gallium (Ga), indium (In), tin (Sn), and silicon (Si). Meanwhile, among these atoms "B", in order to obtain 1,5-pentanedil with a high reaction selectivity thereto, at least one atom selected from the group consisting of zinc, iron, aluminum, and silicon is preferable; while at least one atom selected from the group consisting of zinc, aluminum, and silicon is more preferable, though zinc is further preferably used.

Accordingly, in the reaction of the present invention, for example, in order to obtain an alkanediol having the hydroxy groups at the both molecular terminals thereof with a high reaction electivity thereto, the mass ratio of the copper atom to the atom "B" (copper atom/atom "B") in the metal catalyst to be used therein is usually in the range of 10/90 to 99/1, more preferably in the range of 20/80 to 99/1, still more preferably in the range of 30/70 to 95/5, further still more preferably in the range of 40/60 to 95/5, or particularly preferably in the range of 45/55 to 90/10. Here, the said mass ratio is the content ratio of the metal atoms in the metal catalyst.
Atom "C":

The metal catalyst used in the present invention may further contain as the co-existing atom, in addition to the foregoing atom "B", at least one atom "C" selected from the group consisting of aluminum (Al), barium (Ba), calcium (Ca), manganese (Mn), iron (Fe), nickel (Ni), magnesium (Mg), lanthanum (La), zirconium (Zr), cerium (Ce), and cobalt (Co). However, the atom "C" shall be selected from different atoms other than the atoms "B". Here, as to the atom "C", at least one atom selected from the group consisting of barium, calcium, manganese, lanthanum, cerium, iron, and magnesium is preferable; while at least one atom selected from the group consisting of barium, calcium, manganese, lanthanum, cerium, and magnesium is used more preferably. Among them, in order to obtain a high reaction selectivity, a combination of copper atom, zinc atom, and atom "C", or a combination of copper atom, silicon atom, and atom "C" is especially preferable. Accordingly, by using a metal catalyst further containing atom "C", i.e., if a metal catalyst containing copper atom, atom "B", and atom "C", is used in the reaction of the present invention, an alkanediol having the hydroxy groups at the both molecular terminals thereof can be obtained with a further higher reaction selectivity thereto.

Accordingly, in the reaction of the present invention, in order to obtain an alkanediol having hydroxy groups at both molecular terminals thereof with a high reaction selectivity thereto, for example, content of the atom "C" is, as the mass ratio of the copper atom and the atom "B" to the atom "C" in the metal catalyst to be used therein (sum of copper atom and atom "B"/atom "C"), usually in the range of 10/90 to 99/1, preferably in the range of 30/70 to 95/5, more preferably in the range of 40/60 to 95/5, or particularly preferably in the range of 45/55 to 95/5. Here, the said mass ratio is the content ratio of the metal atoms in the metal catalyst.
Supported Metal Catalyst:

The metal catalyst of the present invention includes a supported metal catalyst in which metal atoms containing the foregoing copper atom and co-existing atoms are supported on a carrier.

In the supported metal catalyst of the present invention, the carrier thereof is not particularly limited; however, preferably used is at least one carrier selected from the group consisting of zinc oxide, silica, alumina, silica alumina (aluminosilicate), ceria, magnesia, calcia, titania, silica titania (titanosilicate), zirconia, active carbon, zeolite, and mesoporous material (mesoporous alumina, mesoporous silica, mesoporous carbon). Moreover, the foregoing carrier is preferably porous in view of the reaction efficiency.

Content of copper atom (Cu) in the supported metal catalyst of the present invention is preferably in the range of 0.1 to 99.9% by mass, more preferably in the range of 1 to 90% by mass, still more preferably in the range of 5 to 80% by mass, or particularly preferably in the range of 10 to 80% by mass.

From the foregoing discussion, as the metal catalyst to be used in the present invention;
a metal catalyst containing copper atom and at least one atom "B" selected from the group consisting of magnesium (Mg), calcium (Ca), barium (Ba), lanthanum (La), cerium (Ce), titanium (Ti), zirconium (Zr), vanadium (V), niobium (Nb), molybdenum (Mo), tungsten (W), manganese (Mn), rhenium (Re), iron (Fe), cobalt (Co), osmium (Os), zinc (Zn), aluminum (Al), gallium (Ga), indium (In), tin (Sn), and silicon (Si); or a supported metal catalyst containing these metals supported on one carrier selected from the group consisting of zinc oxide, silica, alumina, titania, zirconia, and activated carbon are preferred; a metal catalyst containing copper atom, zinc atom, and at least one atom "C" selected from the group consisting of barium (Ba), calcium (Ca), manganese (Mn), iron (Fe), lanthanum (La), and magnesium (Mg); or a supported metal catalyst containing these metals supported on one carrier selected from the group consisting of zinc oxide, silica, alumina, titania, zirconia, and activated carbon are more preferred;
a metal catalyst selected from the group consisting of a copper-zinc type metal catalyst, a copper-zinc-aluminum type metal catalyst, a copper-zinc-iron type metal catalyst, a copper-zinc-silicon type metal catalyst, a copper-zinc-barium type metal catalyst, a copper-zinc-calcium type metal catalyst, a copper-zinc-manganese type metal catalyst, a copper-zinc-manganese-barium type metal catalyst, a copper-zinc-lanthanum type metal catalyst, a copper-zinc-lanthanum-barium type metal catalyst, a copper-zinc-barium-manganese-lanthanum type metal catalyst, a copper-zinc-cerium type metal catalyst, a copper-zinc-magnesium type metal catalyst, a copper-aluminum type metal catalyst, a copper-aluminum-iron type metal catalyst, a copper-aluminum-silicon type metal catalyst, a copper-aluminum-barium type metal catalyst, a copper-aluminum-calcium type metal catalyst, a copper-aluminum-manganese type metal catalyst, a copper-aluminum-manganese-barium type metal catalyst, a copper-aluminum-lanthanum type metal catalyst, a copper-aluminum-lanthanum-barium type metal catalyst, a copper-aluminum-cerium type metal catalyst, a copper-aluminum-magnesium type metal catalyst, a copper-silicon type metal catalyst, a copper-silicon-iron type metal catalyst, a copper-silicon-aluminum type metal catalyst, a copper-silicon-barium type metal catalyst, a copper-silicon-calcium type metal catalyst, a copper-silicon-manganese type metal catalyst, a copper-silicon-manganese-barium type metal catalyst, a copper-silicon-lanthanum type metal catalyst, a copper-silicon-lanthanum-barium type metal catalyst, a copper-silicon-cerium type metal catalyst, and a copper-silicon-magnesium type metal catalyst are still more preferred.

Meanwhile, the above-mentioned metal catalysts are preferably oxides or carbonate salts which contain copper atom and co-existing atoms (atom "B", and atom "B" and further atom "C"). For example, the above-mentioned copper-zinc-barium type metal catalysts are preferably oxides which contain copper atom, zinc atom, and barium atom, or carbonate salts which contain the same atoms.

Form of the Metal Catalyst:

Specific surface area of the metal catalyst of the present invention is preferably in the range of 1 to 1000 m$^2$/g, more preferably in the range of 5 to 500 m$^2$/g, or particularly preferably in the range of 5 to 300 m$^2$/g.

The average pore diameter of the carrier is preferably in the range of 10 to 500 Å, or more preferably in the range of 100 to 250 Å. Meanwhile, the specific surface area of the metal catalyst of the present invention is measured by the BET method; and the average pore diameter thereof is measured by the mercury intrusion method. Particle size of the metal catalyst of the present invention is not particularly limited. The metal catalysts of the present invention that are commercially available may be used as they are, provided that they satisfy the above ranges; or alternatively, they may be obtained by adjusting the composition ratio of copper atom to other metal atoms by a heretofore known method.

Method for Preparing the Metal Catalysts:

Metal catalysts of the present invention may be prepared as follows: firstly, insoluble carbonate salts (catalyst precursor) which contain copper and atom "B" and/or atom "C" are precipitated by the co-precipitation method in the liquid phase, and then, the obtained precipitates are washed, dried, and then calcined.

More specific preparation method is as follows: firstly, an aqueous solution containing a soluble copper salt and soluble salt(s) of atom "B" and/or atom "C" is mixed with an aqueous solution of a precipitant containing an alkaline carbonate or an alkaline bicarbonate, and then, the precipitate thus obtained was separated by filtration, decantation, or the like to obtain insoluble carbonates which contain copper and atom "B" and/or atom "C". As to the soluble copper salt and the soluble salt(s) of atom "B" and/or atom "C", they are not particularly limited, provided that each of them is soluble in water. Therefore, example of the soluble copper salt includes inorganic acid salts of copper such as copper nitrate, copper sulfate, and copper chloride; an organic acid salt of copper, such as copper acetate; and an ammine complex of copper, such as tetra-ammine copper nitrate salt. Example of the soluble salt of atom "B" or atom "C" includes inorganic salts containing atom "B" or atom "C", such as nitrate salts, sulfate salts, and chloride salts thereof; organic acid salts containing atom "B" or atom "C", such as acetate salts and oxalate salts thereof; and ammine complex containing atom "B" or atom "C", such as tetra-ammine nitrate salt thereof. Example of the alkaline carbonate preferably used as the precipitant includes sodium carbonate, potassium carbonate, and ammonium carbonate; and example of the alkaline hydrogencarbonate includes sodium hydrogencarbonate, potassium hydrogencarbonate, and ammonium hydrogencarbonate. Meanwhile, the use rate of the soluble copper salt and the soluble salt of the atom "B" or the atom "C" is not particularly limited because this rate is dependent on the actual reactivity and on the filterability thereof.

Temperature when mixing the aqueous solution containing the precipitant with the aqueous solution containing soluble salts of copper and of atom "B" and/or atom "C" is in the range of 60 to 95° C., or preferably in the range of 60 to 90° C. If this temperature is too low, crystallinity of the insoluble salts which contain copper atom and atom "B" and/or atom "C" is so low that both activity and filterability of the calcined catalyst may become poor; on the other hand, if this temperature is too high, partially oxidized copper, and hydroxides of copper and atom "B" or atom "C", in addition to the objective carbonate salts, may be formed to contaminate the precipitate thereby leading to poor filterability of the calcined catalyst; and thus, these temperatures are not desirable.

Further, pH at the time when mixing the aqueous solution containing the soluble copper salt and the soluble zinc salt and/or the aqueous solution containing the precipitant is kept preferably in the range of 6.5 to 9.0 by adjusting the addition amount of the aqueous solution containing the precipitant. If the pH thereat is too low, basic salts containing anions derived from used metal salts, such as, for example, basic copper nitrate and basic copper sulfate are formed to cause poor activity and filterability of the catalyst that are calcined thereafter; on the other hand, if the pH thereat is too high, amount of the precipitate may be reduced, or copper oxide may partly contaminate the precipitate to cause poor filterability of the catalyst that are calcined thereafter; and thus, these cases are not feasible. After completion of mixing of the foregoing solutions, for aging insoluble carbonate salts thus obtained, it is preferable that the reaction solution be kept at the aforementioned temperature with stirring or be allowed to become cool. Meanwhile, even if the pH thereof changes slightly during this operation, adjustment of the pH is not especially necessary.

The precipitate formed by the afore-mentioned operation is separated by filtration, decantation, or the like, and then washed to obtain it as the insoluble carbonate salts which contain copper and atom "B" and/or atom "C". The insoluble carbonate salts (catalyst precursor) thus obtained may be used as they are, or after they are dried in an air or in an inert gas such as a nitrogen gas at 100 to 120° C., as the metal catalyst for such reactions as the reaction of the present invention and the hydrogenation reaction to produce an alcohol or a diol compound from an ester compound by using hydrogen; however, it is preferable that the metal catalyst containing therein copper and atom "B" and/or atom "C" be prepared by burning it as mentioned later so as to be used for the reaction of the present invention.

The afore-mentioned catalyst precursor is calcined in an air or in an inert gas such as a nitrogen gas to obtain the catalyst of the present invention containing copper and atom "B" and/or atom "C" as the main components therein. The burning temperature is in the range of 200 to 600° C. or preferably in the range of 300 to 450° C. Meanwhile, the metal catalyst to be used in the present invention includes the catalyst that is treated under a reducing atmosphere such as, for example, with hydrogen and carbon monoxide.

It must be noted here that among the metal catalysts prepared by the method as mentioned above, the metal catalysts prepared by using the catalyst precursors containing as the main components therein carbonates which contain, in addition to copper and zinc, at least one atom selected from the group consisting of barium, calcium, lanthanum, manganese, zirconium, and cerium are novel catalysts. These catalyst precursors are preferably insoluble metal salts containing copper, zinc and at least one atom selected from the group consisting of barium, calcium, lanthanum, manganese, zirconium, and cerium, in which the insoluble metal salts is obtainable by mixing an aqueous solution containing a soluble copper salt; and an aqueous solution containing a soluble salt of zinc and a soluble salt at least atom selected from the group consisting of barium, calcium, lanthanum, manganese, zirconium, and cerium; and an aqueous solution containing an alkaline carbonate or an alkaline hydrogencarbonate under the conditions of the temperature of 60 to 95° C. and pH of 6.5 to 9.0.

From the above-mentioned, metal catalysts prepared by using catalyst precursors containing mainly carbonate salts which contain copper, zinc and at least one atom "c1" selected from the group consisting of barium, calcium, manganese, lanthanum, zirconium, and cerium are preferable in viewpoint of high selectivity. In these metal catalysts, metal atom ratios of the respective components are preferably in the range of 40/60 to 60/40 as the mass ratio of copper (Cu) to zinc (Zn) (copper (Cu)/zinc (Zn)); and preferably in the range of 99/1 to 30/70, or more preferably in the range of 99/1 to 80/20 as the mass ratio of copper (Cu) and zinc (Zn) to atom "c1" (copper (Cu) and zinc (Zn)/atom "c1"). Meanwhile, the metal catalysts having the compositions and the respective ratios as mentioned above are useful not only for proceeding the hydrogenolysis reaction of the present invention but also similarly as various hydrogenation catalysts including for the method to produce an alcohol or a diol compound from an ester compound by using hydrogen.

The metal catalysts prepared by using the catalyst precursors containing mainly carbonate salts which contain copper, zinc and at least one atom "c2" selected from the group consisting of calcium, lanthanum, and manganese are preferable in viewpoint of high selectivity. In these metal catalysts, metal atom ratios of the respective components are preferably in the range of 40/60 to 60/40 as the mass ratio of copper (Cu) to zinc (Zn) (copper (Cu)/zinc (Zn)); and preferably in the range of 99/1 to 80/20 as the mass ratio of copper (Cu) and zinc (Zn) to atom "c2" (copper (Cu) and zinc (Zn)/atom "c2"). Meanwhile, the metal catalysts having the compositions and the respective ratios as mentioned above are useful not only for proceeding the hydrogenolysis reaction of the present invention but also similarly as various hydrogenation catalysts including for the method to produce an alcohol or a diol compound from an ester compound by using hydrogen.

The metal catalysts prepared by using the catalyst precursors containing mainly carbonate salts which contain copper, zinc and at least one atom "c3" selected from the group consisting of zirconium and cerium are preferable in viewpoint of high selectivity. In these metal catalysts, metal atom ratios of the respective components are preferably in the range of 40/60 to 60/40 as the mass ratio of copper (Cu) to zinc (Zn) (copper (Cu)/zinc (Zn)); and preferably in the range of 99/1 to 90/10 as the mass ratio of copper (Cu) and zinc (Zn) to atom "c3" (copper (Cu) and zinc (Zn)/atom "c3"). Meanwhile, the metal catalysts having the compositions and the respective ratios as mentioned above are useful not only for proceeding the hydrogenolysis reaction of the present invention but also similarly as various hydrogenation catalysts including for the method to produce an alcohol or a diol compound from an ester compound by using hydrogen.

The metal catalysts prepared by using the catalyst precursors containing mainly carbonate salts which contain, in addition to copper, zinc, and barium, manganese or lanthanum are preferable in viewpoint of high selectivity. In these metal catalysts, as metal atom ratios of the respective components, the mass ratio of copper (Cu) to zinc (Zn) (copper (Cu)/zinc (Zn)) is preferably in the range of 40/60 to 60/40; the mass ratio of copper (Cu) and zinc (Zn) to barium (Ba) (copper (Cu) and zinc (Zn)/barium (Ba)) is preferably in the range of 99/1 to 70/30; the mass ratio of copper (Cu) and zinc (Zn) to manganese (Mn) or lanthanum (La) ([copper (Cu) and zinc (Zn)]/[manganese (Mn) or lanthanum (La)]) is preferably in the range of 99/1 to 80/20. Meanwhile, the metal catalysts having the compositions and the respective ratios as mentioned above are useful not only for proceeding the hydrogenolysis reaction of the present invention but also similarly as various hydrogenation catalysts including for the method to produce an alcohol or a diol compound from an ester compound by using hydrogen.

The metal catalysts obtainable by using the catalyst precursors containing mainly carbonate salts which contain copper, zinc, barium, manganese, and lanthanum are preferable in viewpoint of high selectivity. In these metal catalysts, as metal atom ratios of the respective components, the mass ratio of copper (Cu) to zinc (Zn) (copper (Cu)/zinc (Zn)) is preferably in the range of 40/60 to 60/40; the mass ratio of copper (Cu) and zinc (Zn) to barium (Ba) ([copper (Cu) and zinc (Zn)]/barium (Ba)) is preferably in the range of 99/1 to 70/30, or more preferably in the range of 99/1 to 80/20; the mass ratio of copper (Cu), zinc (Zn), and barium (Ba) to manganese and lanthanum ([copper (Cu), zinc (Zn), and barium (Ba)]/[manganese (Mn) and lanthanum (La)]) is preferably in the range of 99/1 to 70/30, or more preferably in the range of 99/1 to 80/20. Meanwhile, the metal catalysts having the compositions and the respective ratios as mentioned above are useful not only for proceeding the hydrogenolysis reaction of the present invention but also similarly as various hydrogenation catalysts including for the method to produce an alcohol or a diol compound from an ester compound by using hydrogen.

The metal catalysts prepared by using the catalyst precursors containing mainly carbonate salts which contain copper, zinc, and barium are preferable in viewpoint of high selectivity. In these metal catalysts, as metal atom ratios of the respective components, the mass ratio of copper (Cu) to zinc (Zn) (copper (Cu)/zinc (Zn)) is preferably in the range of 40/60 to 60/40; the mass ratio of copper (Cu) and zinc (Zn) to barium (Ba) (copper (Cu) and zinc (Zn)/barium (Ba)) is preferably in the range of 99/1 to 70/30. Meanwhile, the metal catalysts having the compositions and the respective ratios as mentioned above are useful not only for proceeding the hydrogenolysis reaction of the present invention but also similarly as various hydrogenation catalysts including for the method to produce an alcohol or a diol compound from an ester compound by using hydrogen.

On the other hand, the supported metal catalysts of the present invention may be used as they are if they are commercially available. They may be also prepared by the method, for example, as following; water is removed from a mixture of an aqueous solution or slurry containing at least copper compound selected from the group consisting of copper, copper oxide, copper iodide, copper bromide, copper chloride, copper fluoride, copper sulfate, copper nitrate, copper salts of organic sulfonic acids, such as copper methanesulfonate salt and copper trifluoromethanesulfonate salt, and copper organic carboxylate salt compounds, such as copper acetate and copper propionate; an aqueous solution or slurry containing metal compound selected from the group consisting of oxides, iodides, bromides, chlorides, fluorides, sulfate salts, and nitrate salts, copper organic sulfonic acid salts, such as methanesulfonate salt, trifluoromethanesulfonate salt, and organic carboxylate salts, such as copper acetate and copper propionate, of at least one atom "B" selected from the elements of the third to the sixth periods of the II to XIV groups (excluding chromium) in the periodical table; and a carrier impregnated, and then, the solid thereby obtained is calcined. Meanwhile, use amounts of the copper compounds and the metal compounds containing other metal atoms may be adjusted appropriately in accordance with the intended blending ratios. As to water to be used for preparation of the aqueous solution of the copper compounds, for example, pure water, ultrapure water, ion-exchanged water, or the like may be used, wherein use amount thereof is not particularly limited.

Preparation method of the supported metal catalyst of the present invention is different depending on the kind and the like of the copper compound and/or the other metal compounds to be used; for example, the said catalyst may be obtained with the preparation time of 0.1 to 20 hours and by evaporating water from the aqueous solution or the slurry mentioned before. The burning temperature is preferably in the range of −5 to 800° C., or more preferably in the range of 100 to 500° C.

Meanwhile, the metal catalyst or the supported metal catalyst of the present invention is useful not only for the hydrogenolysis reaction of the present invention but also similarly as the hydrogenation catalyst including for a method to produce an alcohol or a diol compound from an ester compound by using hydrogen.

Use Amount of the Metal Catalyst:

In the reaction of the present invention, each of the metal catalysts of the present invention may be used solely or as a mixture of two or more of them; or alternatively, the catalyst containing copper atom and other metal atoms and the supported metal catalyst may be used together. In the case when the reaction style (reaction system) is a liquid phase slurry reaction, use amount (total) of the metal catalyst is preferably in the range of 0.01 to 50% by mass, more preferably in the range of 0.01 to 20% by mass, still more preferably in the range of 0.05 to 10% by mass, or particularly preferably in the range of 0.1 to 5% by mass, relative to the cyclic ether group-containing methanol. In the case when the reaction style (reaction system) is a fixed-bed flow reaction, use amount of the metal catalyst and feed amount of the cyclic ether group-containing methanol are controlled such that the space time yield (STY) may become in the range of 1 to 5000 g/liter-hour, preferably in the range of 10 to 1000 g/liter-hour, or more preferably in the range of 50 to 500 g/liter-hour. Within the above ranges, the alkanediol having the hydroxy groups at the both molecular terminals thereof can be obtained with a high reaction selectivity thereto and with a higher yield.

Hydrogen to be Used in the Present Invention

The method for producing the alkanediol shown by the formula (2) of the present invention is carried out by using hydrogen. Amount of hydrogen to be used is not particularly limited provided that the amount thereof is equivalent or more in terms of mole relative to the cyclic ether group-containing methanol shown by the formula (1). Meanwhile, it is preferable that the reaction of the present invention be carried out under a hydrogen gas atmosphere (under the hydrogen pressure), wherein the hydrogen pressure thereat is preferably in the range of an atmospheric pressure to 50 MPa, more preferably in the range of 1 to 40 MPa, still more preferably in the range of 10 to 38 MPa, or particularly preferably in the range of 15 to 35 MPa.

Reaction Solvent

In the production method of the present invention, a reaction solvent may be used, for example, in order to adjust dispersion of the metal catalyst or to increase solubility of the cyclic ether group-containing methanol such as tetrahydrofurfuryl alcohol and/or the product alkanediol having the hydroxy groups at the both molecular terminals thereof such as 1,5-pentanediol; however, in the present invention, it is preferable that the reaction be carried out without using a reaction solvent.

Kind of the Reaction Solvent:

However, in the case that the reaction solvent is necessary, example of the reaction solvent to be used includes water; alcohols, such as methanol, ethanol, 1-propanol, 2-propanol, n-butanol, t-butanol, and ethylene glycol; hydrocarbons, such as heptane, hexane, cyclohexane, benzene, and toluene; amides, such as N,N-dimethylformamide, N,N-dimethylacetamide, and N-methyl-2-pyrrolidone; and halogenated aliphatic hydrocarbons, such as methylene chloride and dichloroethane. These reaction solvents may be used singly or as a mixture of two or more of them.

Use Amount of the Reaction Solvent:

Use amount of the foregoing reaction solvent is preferably in the range of 0.05 to 100 g, or more preferably in the range of 0.1 to 20 g, relative to 1 g of the cyclic ether group-containing methanol of the present invention.

Reaction Conditions

Reaction Style:

The reaction method (manufacturing equipment and manufacturing apparatus) of the present invention may be any of a continuous method and a batch method; and the reaction style (reaction system) may be any of a liquid phase slurry reaction and a gas phase reaction such as a fixed-bed flow reaction.

Reaction Temperature and Reaction Pressure:

Reaction temperature in the reaction of the present invention is preferably in the range of 25 to 450° C., more preferably in the range of 150 to 400° C., or still more preferably in the range of 200 to 350° C. Meanwhile, the reaction of the present invention is carried out under the hydrogen pressure; and thus, the reaction pressure is in the same range as those of the before-mentioned hydrogen pressure.

Reaction Time:

Reaction time in the present invention is dependent on the reaction temperature, the reaction pressure, concentration of the substrate (concentration of the cyclic ether group-containing methanol shown by the formula (1)), use amount of the metal catalyst, the reaction equipment, and the like; and thus, the reaction time is not particularly limited. However, in the reaction of the present invention, if the reaction time is prolonged, the conversion thereof can be increased, but on the contrary, products of consecutive reactions as well as decomposition products tend to increase commensurately; and thus, the reaction time is preferably in the range of 0.5 to 14 hours.

Composition of the Reaction Solution:

In the reaction solution containing the alkanediol shown by the formula (2) which is obtained by the production method of the present invention, an alkanediol having a secondary hydroxyl group, such as 1,2-pentanediol, and an alkyl alcohol, such as 1-pentanol, are contained therein as impurities. Contents of the impurities is preferably suppressed such that the reaction selectivity to the alkanediol having a secondary alcohol, such as 1,2-pentanediol, may be 5% or less, preferably 3% or less, more preferably 1% or less, or particularly preferably 0.5% or less, though depending on the capacity of the work-up method after completion of the reaction as mentioned later. In addition, the reaction selectivity to the alkyl alcohol such as 1-pentanol is preferably suppressed to 6% or less, preferably to 4% or less, or particularly preferably to 3% or less.

Work-Up Method after Completion of the Reaction:

The alkanediol shown by the formula (2) that is obtained by the production method of the present invention may also be purified by distillation, a column chromatography, or the like, after the work-up operations such as, for example, filtration, phase separation and extraction, and concentration after completion of the reaction. In view of the production efficiency, it is preferable that the alkanediol obtained by the production method of the present invention be purified by distillation.

The production method of the present invention as mentioned above is established such that both the reaction conversion rate of the raw material cyclic ether group-containing methanol and the reaction selectivity to the alkanediol shown by the formula (2), which is the objective product of the present invention, may be high; and thus, the alkanediol shown by the formula (2) such as 1,5-pentanediol may be produced industrially suitably.

EXAMPLES

Next, the present invention will be explained specifically by showing Examples; but the present invention is not limited by these Examples.

Meanwhile, in the present Examples, all of qualitative and quantitative analyses of the consumed amount of the raw material tetrahydrofurfuryl alcohol (cyclic ether group-containing methanol), the produced amount of the product 1,5-pentanediol (alkanediol having the hydroxy groups at the both molecular terminals thereof; hereinafter this is sometimes referred to as "alkanediol of the present invention"), and so forth were made with a gas chromatography (GC) by using GC-2010 (manufactured by Shimadzu Corp., GC column: InertCap WAX 30 m×0.53 mm, GC detector: FID, internal standards: any of dimethyl glutarate, 1-octanol, and triethylene glycol was used). Meanwhile, the reaction conversion rate of the raw material tetrahydrofurfuryl alcohol (cyclic ether group-containing methanol), the reaction selectivity to the objective product 1,5-pentanediol (alkanediol of the present invention), and the reaction yield thereof each was calculated by using the following equations (A) to (C). The selectivities to the respective impurities were calculated by substituting the alkanediol of the present invention to the respective impurities in the equation (B).

Preparation Method of Copper-Atom "B" Catalysts

Reference Example 1

Copper-Zinc Catalyst

An aqueous metal salt solution was prepared by dissolving 48.6 g of cupric (II) nitrate trihydrate (12.8 g as copper) and 58.2 g of zinc (II) nitrate hexahydrate (12.8 g as zinc) into 130.3 g of deionized water. Separately, 63.3 g of sodium carbonate (anhydrous) was dissolved into 261.8 g of deionized water to prepare a basic aqueous solution. Further separately, 160.5 g of deionized water whose temperature was adjusted at 75 to 85° C. was put in a vessel equipped with a stirring blade, a thermometer, and a pH electrode; and then, into this solution were dropped the aqueous metal salt solution and the basic aqueous solution at the same time while keeping the formed mixture solution at pH of 7.0 to 7.5 and the temperature of 75 to 85° C. During dropping, material having a pale green color was precipitated. After completion of the reaction, the precipitated material was collected by filtration, and then washed with 700 mL of deionized water to obtain a wet solid. The solid thereby obtained was dried at 120° C. to obtain 41.0 g of green powders (catalyst precursor). Thereafter, 10.0 g of the powders thus obtained were calcined in an air at 350° C. for 2 hours to obtain 7.7 g of the copper-zinc as black powders.

Preparation of Alkanediol by Using Copper-Atom "B" Catalysts

Example 1

Synthesis of 1,5-Pentanediol; Copper-Zinc Type Metal Catalyst

Into a 100-mL autoclave were taken 20 g tetrahydrofurfuryl alcohol (0.196 mole) and 2.0 g of the copper-zinc type metal catalyst (prepared by the method described in Refer- $$\text{Reaction conversion of cyclic ether group-containing methanol (\%)} = \frac{([\text{consumption of cyclic ether group-containing (mole)}]^{*1})}{[\text{use amount of cyclic group-containing methanol (mole)}]} \times 100\% \quad \text{Equation (A)}$$

*1 By quantitative analyses (GC), the above-mentioned consumption or use amount was calculated in terms of mole.

$$\text{Reaction selectivity to } alkanediol \text{ of the present invention (\%)} = \frac{([\text{produced amount of } alkanediol \text{ of the present invention (mole)}]^{*1})}{[\text{consumption of cyclic ether group-containing methanol(mole)}]} \times 100 \, (\%) \quad \text{Equation (B)}$$

*1 By quantitative analyses (GC), the above-mentioned consumption or use amount was calculated in terms of mole.

$$\text{Reaction yield of } alkanediol \text{ of the present invention (\%)} = \frac{\text{reaction conversion of cyclic ether group-containing methanol (\%)} \times \text{reaction selectivity to } alkanediol \text{ of the present invention (\%)}}{100(\%)} \quad \text{Equation (C)}$$

ence Example 1; metal component ratio of Cu/Zn=50/50; 10% by mass relative to the use amount of tetrahydrofurfuryl alcohol); and then, after atmosphere inside the autoclave was displaced by gases, for 5 times by a nitrogen gas and then for 5 times by a hydrogen gas, the autoclave was filled with a hydrogen gas till the inner pressure thereof reached 15 MPa. Then, after the reaction temperature was made to 250° C., a hydrogen gas was charged till the inner pressure of the autoclave reached 25 MPa, and then the reaction was carried out for 7 hours. After completion of the reaction, the reaction solution was allowed to be cooled to room temperature; and then, after the autoclave was opened, the obtained reaction solution was quantitatively analyzed by a gas chromatography to find that the objective product 1,5-pnetanediol was obtained with the reaction selectivity of 97.6% thereto, with 37.4% of the reaction conversion of tetrahydrofurfuryl alcohol (reaction yield of 36.5%).

It was found that the reaction yield of the by-produced 1-pentanol was 0.9% (reaction selectivity of 2.5%), and the reaction yield of 1,2-pentanediol was 0.05% (reaction selectivity of 0.1%). These results are shown in Table 1.

Example 2

Synthesis of 1,5-Pentanediol; Copper-Zinc Type Metal Catalyst

Into a 100-mL autoclave were taken 20 g tetrahydrofurfuryl alcohol (0.196 mole) and 2.0 g of the copper-zinc type metal catalyst (prepared by the method described in Reference Example 1; metal component ratio of Cu/Zn=50/50; use amount of 10% by mass relative to tetrahydrofurfuryl alcohol); and then, after atmosphere inside the autoclave was displaced by gases, for 5 times by a nitrogen gas and then for 5 times by a hydrogen gas, the autoclave was filled with a hydrogen gas till the inner pressure thereof reached 15 MPa. Then, after the reaction temperature was made to 270° C., a hydrogen gas was charged till the inner pressure of the autoclave reached 25 MPa, and then the reaction was carried out for 5 hours. After completion of the reaction, the reaction solution was allowed to be cooled to room temperature; and then, after the autoclave was opened, the obtained reaction solution was quantitatively analyzed by a gas chromatography to find that the objective product 1,5-pnetanediol was obtained with the reaction selectivity of 95.1% thereto, with 55.2% of the reaction conversion of tetrahydrofurfuryl alcohol (reaction yield of 52.5%).

It was found that the reaction yield of the by-produced 1-pentanol was 2.3% (reaction selectivity of 4.2%), the reaction yield of δ-valerolactone was 0.2%, and the reaction yield of 1,2-pentanediol was 0.03% (reaction selectivity of 0.1%). These results are shown in Table 1.

Example 3

Synthesis of 1,5-Pentanediol; Copper-Zinc Type Metal Catalyst

Into a 100-mL autoclave were taken 20 g tetrahydrofurfuryl alcohol (0.196 mole) and 2.0 g of the copper-zinc type metal catalyst (prepared by the method described in Reference Example 1; metal component ratio of Cu/Zn=50/50; use amount of 10% by mass relative to tetrahydrofurfuryl alcohol); and then, after atmosphere inside the autoclave was displaced by gases, for 5 times by a nitrogen gas and then for 5 times by a hydrogen gas, the autoclave was filled with a hydrogen gas till the inner pressure thereof reached 13 MPa. Then, after the reaction temperature was made to 240 to 250° C., a hydrogen gas was charged till the inner pressure of the autoclave reached 20 MPa, and then the reaction was carried out for 7 hours. After completion of the reaction, the reaction solution was allowed to be cooled to room temperature; and then, after the autoclave was opened, the obtained reaction solution was quantitatively analyzed by a gas chromatography to find that the objective product 1,5-pnetanediol was obtained with the reaction selectivity of 96.5% thereto, with 31.9% of the reaction conversion of tetrahydrofurfuryl alcohol (reaction yield of 30.8%).

It was found that the reaction yield of the by-produced 1-pentanol was 0.9% (reaction selectivity of 2.8%), the reaction yield of δ-valerolactone was 0.2%, and the reaction yield of 1,2-pentanediol was 0.04% (reaction selectivity of 0.1%). These results are shown in Table 1.

Comparative Example 1

Synthesis of 1,5-Pentanediol; Copper-Chromium-Manganese Type Metal Catalyst

The procedure of Example 1 was repeated to carry out the reaction, except that 2.0 g of the copper-chromium-manganese type metal catalyst N202D (product name, manufactured by JGC Catalysts and Chemicals, Ltd.) was used with the amount thereof being 10% by mass relative to tetrahydrofurfuryl alcohol, in place of the copper-zinc type metal catalyst used in Example 1. After completion of the reaction, the obtained reaction solution was quantitatively analyzed by a gas chromatography to find that the objective product 1,5-pnetanediol was obtained with the reaction selectivity of 81.8% thereto, with 12.1% of the reaction conversion of tetrahydrofurfuryl alcohol (reaction yield of 9.9%).

It was found that the reaction yield of the by-produced 1-pentanol was 0.3% (reaction selectivity of 2.2%), the reaction yield of 1,2-pentanediol was 0.05% (reaction selectivity of 0.5%), and δ-valerolactone was below the detection limit of the gas chromatography. These results are shown in Table 1.

TABLE 1

Table 1-1

| Example/Comparative Example | Metal catalyst | Catalyst addition amount (% by mass) | Hydrogen gas (MPa) | Reaction Temperature (° C.) | Reaction time (h) |
| --- | --- | --- | --- | --- | --- |
| Example 1 | Cu—Zn | 10 | 25 | 250 | 7 |
| Example 2 | Cu—Zn | 10 | 25 | 270 | 5 |
| Example 3 | Cu—Zn | 10 | 20 | 250 | 7 |
| Comparative Example 1 | Cu—Cr—Mn | 10 | 25 | 250 | 5 |

TABLE 1-continued

Table 1-2

| Example/Comparative Example | THFA *1 Conversion rate (% by mass) | 1,5-PDL *2 Yield (%) | 1,5-PDL *2 Selectivity (%) | 1-PeOH *3 Selectivity (%) | 1,2-PDL *4 Selectivity (%) | δ-VL *5 Selectivity (%) |
|---|---|---|---|---|---|---|
| Example 1 | 37.4 | 36.5 | 97.6 | 2.4 | 0.1 | N.D.*6 |
| Example 2 | 55.2 | 52.5 | 95.1 | 4.2 | 0.1 | 0.4 |
| Example 3 | 31.9 | 30.8 | 96.5 | 2.8 | 0.1 | 0.5 |
| Comparative Example 1 | 12.1 | 9.9 | 81.8 | 2.2 | 0.5 | N.D.*6 |

*1 Tetrahydrofurfuryl alcohol
*2 1,5-pentanediol
*3 1-pentanol
*4 1,2-pentanediol
*5 δ-valerolactone
*6 N.D.: below detection limit

Example 4

Synthesis of 1,5-Pentanediol

Into a 200-mL autoclave were taken 100 g tetrahydrofurfuryl alcohol (0.979 mole) and 2.0 g of the copper-zinc type metal catalyst (prepared by the method described in Reference Example 1; metal composition ratio of Cu/Zn=50/50; use amount of 2% by mass relative to tetrahydrofurfuryl alcohol); and then, after atmosphere inside the autoclave was displaced by gases, for 5 times by a nitrogen gas and for 5 times by a hydrogen gas, the autoclave was filled with a hydrogen gas till the inner pressure thereof reached 15 MPa. Then, after the reaction temperature was made to 270° C., a hydrogen gas was charged till the inner pressure of the autoclave reached 25 MPa, and then the reaction was carried out for 5 hours. After completion of the reaction, the reaction solution was allowed to be cooled to room temperature; and then, after the autoclave was opened, the obtained reaction solution was quantitatively analyzed by a gas chromatography to find that the objective product 1,5-pnetanediol was obtained with the reaction selectivity of 94.1% thereto, with 19.5% of the reaction conversion of tetrahydrofurfuryl alcohol (reaction yield of 18.4%).

It was found that the reaction yield of the by-produced 1-pentanol was 0.7% (reaction selectivity of 3.4%), and the reaction yield of 1,2-pentanediol was 0.06% (reaction selectivity of 0.3%). These results are shown in Table 2.

Example 5 to Example 7

Synthesis of 1,5-Pentanediol

The procedure of Example 4 was repeated, except that the reaction conditions were changed to those shown in Table 2, to carry out the reaction of tetrahydrofurfuryl alcohol with hydrogen by using the metal catalyst (copper-atom "B" catalyst). These results are shown in Table 2. Meanwhile, the catalyst addition amount in Table 2 is shown in terms of the catalyst content relative to the raw material tetrahydrofurfuryl alcohol (% by mass).

Comparative Example 2

Synthesis of 1,5-Pentanediol

The procedure of Example 5 was repeated, except that the reaction conditions were changed to those shown in Table 2, and that the chromium-containing metal catalyst Cu-0202P (product name, manufactured by N. E. Chemcat Corp.), to carry out the reaction of tetrahydrofurfuryl alcohol with hydrogen. These results are shown in Table 2. Meanwhile, the catalyst addition amount in Table 2 is shown in terms of the catalyst content relative to the raw material tetrahydrofurfuryl alcohol (% by mass).

TABLE 2

Table 2-1

| Example/Comparative Example | Metal catalyst Composition | Metal catalyst Item number | Catalyst addition amount (% by mass) | Hydrogen gas (MPa) | Reaction Temperature (° C.) | Reaction time (h) |
|---|---|---|---|---|---|---|
| Example 4 | Cu—Zn | *1 | 2 | 25 | 270 | 5 |
| Example 5 | Cu—Zn | *1 | 2 | 25 | 285 | 5 |
| Example 6 | Cu—Zn | *1 | 2 | 25 | 300 | 5 |
| Example 7 | Cu—Zn | *1 | 10 | 25 | 285 | 5 |
| Comparative Example 2 | Cu—Cr | Cu-0202P *2 | 2 | 25 | 285 | 5 |

Table 2-2

| Example/Comparative Example | THFA*3 Conversion rate (%) | 1,5-PDL*4 Yield (%) | 1,5-PDL*4 Selectivity (%) | 1-PeOH*5 Selectivity (%) | 1,2-PDL*6 Selectivity (%) |
|---|---|---|---|---|---|
| Example 4 | 19.5 | 18.4 | 94.1 | 3.4 | 0.3 |
| Example 5 | 30.1 | 26.8 | 88.9 | 4.3 | 0.1 |

TABLE 2-continued

| | | | | | |
|---|---|---|---|---|---|
| Example 6 | 49.3 | 41.9 | 85.0 | 5.6 | 0.0 |
| Example 7 | 56.0 | 50.3 | 89.7 | 5.3 | 0.1 |
| Comparative Example 2 | 28.2 | 25.0 | 88.7 | 3.1 | 1.0 |

*1 Prepared by the method described in Reference Example 1
*2 Manufactured by N.E. Chemcat Corp.
*3 Tetrahydrofurfuryl alcohol
*4 1,5-Pentanediol
*5 1-Pentanol
*6 1,2-Pentanediol Preparation of Copper-Atom "B"-Atom "C" Catalyst Example 8

Preparation Method of Metal Catalyst:
Copper-Zinc-Magnesium Catalyst

An aqueous metal salt solution was prepared by dissolving 46.3 g of cupric (II) nitrate trihydrate (12.1 g as copper atom), 57.2 g of zinc (II) nitrate hexahydrate (12.6 g as zinc atom), and 5.6 g of magnesium (II) nitrate hexahydrate (0.53 g as magnesium) into 129.4 g of deionized water (at this time, if some of them remains undissolved, they may be dissolved by heating). Separately, 63.5 g of sodium carbonate (anhydrous) was dissolved into 265.6 g of deionized water to prepare a basic aqueous solution. Further separately, 159.3 g of deionized water whose temperature was adjusted at 75 to 85° C. was arranged in a vessel equipped with a stirring blade, a thermometer, and a pH electrode; and then, into this solution were dropped the aqueous metal salt solution and the basic aqueous solution at the same time while keeping the formed mixture solution at pH of 7.0 to 7.5 and the temperature of 75 to 85° C. During dropping, material having a pale green color was precipitated. After completion of the reaction, the precipitated material was collected by filtration, and then washed with 700 mL of deionized water to obtain a wet solid. The solid thereby obtained was dried at 120° C. to obtain 42.6 g of green powders (catalyst precursor). Thereafter, 20.56 g of the powders thus obtained were calcined in an air at 350° C. for 2 hours to obtain 16.0 g of the Cu—Zn—Mg catalyst as black powders.

Example 9

Preparation Method of Metal Catalyst:
Copper-Zinc-Barium Catalyst

An aqueous metal salt solution was prepared by dissolving 28.9 g of cupric (II) nitrate trihydrate (7.6 g as copper atom), 34.7 g of zinc (II) nitrate hexahydrate (7.6 g as zinc atom), and 7.6 g of barium (II) nitrate (4.0 g as barium) into 259.0 g of deionized water (at this time, if some of them remains undissolved, they may be dissolved by heating). Separately, 42.74 g of sodium carbonate (anhydrous) was dissolved into 178.4 g of deionized water to prepare a basic aqueous solution. Further separately, 105.7 g of deionized water whose temperature was adjusted at 75 to 85° C. was arranged in a vessel equipped with a stirring blade, a thermometer, and a pH electrode; and then, into this solution were dropped the aqueous metal salt solution and the basic aqueous solution at the same time while keeping the formed mixture solution at pH of 7.0 to 7.5 and the temperature of 75 to 85° C. During dropping, material having a pale green color was precipitated. After completion of the reaction, the precipitated material was collected by filtration, and then washed with 700 mL of deionized water to obtain a wet solid. The solid thereby obtained was dried at 120° C. to obtain 30.7 g of pale green powders (catalyst precursor). Thereafter, 15.1 g of the powders thus obtained were calcined in an air at 350° C. for 2 hours to obtain 12.3 g of the Cu—Zn—Ba catalyst as black powders.

Example 10

Preparation Method of Metal Catalyst:
Copper-Zinc-Lanthanum Catalyst

An aqueous metal salt solution was prepared by dissolving 36.9 g of cupric (II) nitrate trihydrate (9.7 g as copper atom), 44.1 g of zinc (II) nitrate hexahydrate (9.7 g as zinc atom), and 6.8 g of lanthanum (III) nitrate hexahydrate (2.2 g as lanthanum) into 103.6 g of deionized water (at this time, if some of them remains undissolved, they may be dissolved by heating). Separately, 50.18 g of sodium carbonate (anhydrous) was dissolved into 249.1 g of deionized water to prepare a basic aqueous solution. Further separately, 130.1 g of deionized water whose temperature was adjusted at 75 to 85° C. was arranged in a vessel equipped with a stirring blade, a thermometer, and a pH electrode; and then, into this solution were dropped the aqueous metal salt solution and the basic aqueous solution at the same time while keeping the formed mixture solution at pH of 7.0 to 7.5 and the temperature of 75 to 85° C. During dropping, material having a pale green color was precipitated. After completion of the reaction, the precipitated material was collected by filtration, and then washed with 700 mL of deionized water to obtain a wet solid. The solid thereby obtained was dried at 120° C. to obtain 36.8 g of pale green powders (catalyst precursor). Thereafter, 20.3 g of the powders thus obtained were calcined in an air at 350° C. for 2 hours to obtain 15.8 g of the Cu—Zn—La catalyst as black powders.

Example 11

Preparation Method of Metal Catalyst:
Copper-Zinc-Manganese-Barium Catalyst

An aqueous metal salt solution was prepared by dissolving 40.3 g of cupric (II) nitrate trihydrate (10.6 g as copper atom), 48.2 g of zinc (II) nitrate hexahydrate (10.6 g as zinc atom), 13.8 g of manganese (II) nitrate hexahydrate (2.6 g as manganese), and 5.1 g barium (II) nitrate (2.7 g as barium) into 138.1 g of deionized water (at this time, if some of them remains undissolved, they may be dissolved by heating). Separately, 63.6 g of sodium carbonate (anhydrous) was dissolved into 259.6 g of deionized water to prepare a basic aqueous solution. Further separately, 160.2 g of deionized water whose temperature was adjusted at 75 to 85° C. was arranged in a vessel equipped with a stirring blade, a thermometer, and a pH electrode; and then, into this solution were dropped the aqueous metal salt solution and the basic aqueous solution at the same time while keeping the formed mixture solution at pH of 7.0 to 7.5 and the temperature of 75 to 85° C. During dropping, material having a pale green color was precipitated. After completion of the reaction, the precipitated material was collected by filtration, and then washed with 700 mL of deionized water to obtain a wet solid. The solid thereby obtained was dried at 120° C. to obtain 43.04 g of pale green powders (catalyst precursor). Thereafter, 20.0 g of the powders thus obtained were calcined in an air at 350° C. for 2 hours to obtain 16.8 g of the Cu—Zn—Mn—Ba catalyst as black powders.

Preparation of Alkanediol by Using Copper-Atom "B"-Atom "C" Catalysts

Example 12 to Example 31 and Comparative Example 3

Synthesis of 1,5-Pentanediol

The procedure of Example 5 was repeated, except that the reaction conditions were changed to those shown in Table 3, to carry out the reaction of tetrahydrofurfuryl alcohol with hydrogen by using metal catalysts (copper-atom "B"-atom "C" catalysts).

Meanwhile, the metal catalysts without item numbers (product codes) in Table 3 were prepared by the preparation procedure described in Example 8 by using the respective nitrate salts of corresponding metal atoms (atom "B" and atom "C"). The mass ratios (content ratio of the metal atoms in the metal catalysts) in the prepared metal catalysts were shown as the catalyst ratio in Table 3. The metal catalyst content relative to the raw material tetrahydrofurfuryl alcohol (% by mass) is shown as the catalyst addition amount in Table 3.

TABLE 3

Table 3-1

| Example/Comparative Example | Metal catalyst Composition | Metal catalyst Item number | Metal catalyst Catalyst ratio (% by mass) | Catalyst addition amount (% by mass) | Hydrogen gas (MPa) | Reaction Temperature (° C.) | Reaction time (h) |
|---|---|---|---|---|---|---|---|
| Example 12 | Cu—Zn—Mg | *1 | 48.5/48.5/3 | 2 | 25 | 285 | 5 |
| Example 13 | Cu—Zn—Ca | *1 | 49/49/2 | 2 | 25 | 285 | 5 |
| Example 14 | Cu—Zn—Ca | *1 | 45/45/10 | 2 | 25 | 285 | 5 |
| Example 15 | Cu—Zn—Ba | *1 | 48.5/48.5/3 | 2 | 25 | 285 | 5 |
| Example 16 | Cu—Zn—Ba | *2 | 40/40/20 | 2 | 25 | 285 | 5 |
| Example 17 | Cu—Zn—Ba | *2 | 50/30/20 | 2 | 25 | 285 | 5 |
| Example 18 | Cu—Zn—Ba | *2 | 25/25/50 | 2 | 25 | 285 | 5 |
| Example 19 | Cu—Zn—Mn | *1 | 48.5/48.5/3 | 2 | 25 | 285 | 5 |
| Example 20 | Cu—Zn—Mn | *1 | 45/45/10 | 2 | 25 | 285 | 5 |
| Example 21 | Cu—Zn—Mn—Ba | *3 | 47/47/3/3 | 2 | 25 | 285 | 5 |
| Example 22 | Cu—Zn—Mn—Ba | *3 | 40/40/10/10 | 2 | 25 | 285 | 5 |
| Example 23 | Cu—Zn—Al | *1 | 48.5/48.5/3 | 2 | 25 | 285 | 5 |
| Example 24 | Cu—Zn—Zr | *1 | 48.5/48.5/3 | 2 | 25 | 285 | 5 |
| Example 25 | Cu—Zn—La | *1 | 48.5/48.5/3 | 2 | 25 | 285 | 5 |
| Example 26 | Cu—Zn—La | *4 | 45/45/10 | 2 | 25 | 285 | 5 |
| Example 27 | Cu—Zn—Ba—La | *3 | 47/47/3/3 | 2 | 25 | 285 | 5 |
| Example 28 | Cu—Zn—Ba—La | *3 | 38.5/38.5/20/3 | 2 | 25 | 285 | 5 |
| Example 29 | Cu—Zn—Ce | *1 | 48.5/48.5/3 | 2 | 25 | 285 | 5 |
| Example 30 | Cu—Al—Mn | T-8706 *5 | — | 2 | 25 | 285 | 5 |
| Example 31 | Cu—Si—Ca | Cu-0860E *6 | — | 2 | 25 | 285 | 5 |
| Comparative Example 3 | Cu—Cr—Mn | N203S *7 | — | 2 | 25 | 285 | 5 |

Table 3-2

| Example/Comparative Example | THFA*8 Conversion rate (%) | 1,5-PDL*9 Yield (%) | 1,5-PDL*9 Selectivity (%) | 1-PeOH*10 Selectivity (%) | 1,2-PDL*11 Selectivity (%) |
|---|---|---|---|---|---|
| Example 12 | 32.6 | 29.5 | 90.5 | 3.1 | 0.1 |
| Example 13 | 34.2 | 32.2 | 94.1 | 2.2 | 0.1 |
| Example 14 | 36.6 | 33.0 | 90.2 | 2.0 | 0.1 |
| Example 15 | 34.5 | 32.0 | 92.8 | 2.2 | 0.1 |
| Example 16 | 41.3 | 38.5 | 93.1 | 2.1 | 0.0 |
| Example 17 | 34.2 | 31.2 | 91.2 | 2.4 | 0.1 |
| Example 18 | 28.9 | 27.1 | 93.9 | 1.0 | 0.0 |
| Example 19 | 34.4 | 31.3 | 91.0 | 2.0 | 0.1 |
| Example 20 | 36.4 | 32.2 | 88.6 | 2.2 | 0.1 |
| Example 21 | 34.9 | 33.1 | 94.9 | 2.0 | 0.1 |
| Example 22 | 31.9 | 28.5 | 89.3 | 1.9 | 0.1 |
| Example 23 | 31.7 | 28.3 | 89.4 | 4.0 | 0.1 |
| Example 24 | 34.6 | 29.8 | 86.3 | 3.8 | 0.1 |
| Example 25 | 52.7 | 47.0 | 89.1 | 1.1 | 0.0 |
| Example 26 | 53.4 | 47.1 | 88.1 | 1.3 | 0.0 |
| Example 27 | 64.8 | 56.5 | 87.1 | 1.1 | 0.0 |
| Example 28 | 62.6 | 57.0 | 91.1 | 1.1 | 0.0 |

TABLE 3-continued

| | | | | | |
|---|---|---|---|---|---|
| Example 29 | 38.4 | 32.6 | 84.9 | 1.6 | 0.1 |
| Example 30 | 38.9 | 36.1 | 92.8 | 2.2 | 0.4 |
| Example 31 | 40.2 | 38.2 | 95.0 | 1.5 | 0.1 |
| Comparative Example 3 | 41.6 | 35.3 | 84.8 | 4.1 | 1.2 |

*1 Prepared according to Example 8
*2 Prepared according to Example 9
*3 Prepared according to Example 11
*4 Prepared according to Example 10
*5 Manufactured by Sud-Chemie AG
*6 Manufactured by N.E. Chemcat Corp.
*7 Manufactured by JGC Catalysts and Chemicals, Ltd.
*8 Tetrahydrofurfuryl alcohol
*9 1,5-Pentanediol
*10 1-Pentanol
*11 1,2-Pentanediol From the above, the present invention enabled to provide a method for producing 1,5-pentanediol with a high reaction selectivity thereto while suppressing production of various by-products including an alkanediol having a secondary hydroxy group such as 1,2-pentanediol and an alkyl alcohol such as 1-pentanol, production of these by-products being observed in conventional methods. In addition, from the above Examples, compounds containing copper, zinc, and barium with the composition ratio thereof being Cu:Zn:Ba=40 to 60:40 to 60:1 to 20 (for example, Example 16 and so forth), compounds containing copper-zinc and at least one atom "C" selected from the group consisting of calcium, lanthanum, and manganese with the composition ratio thereof being Cu:Zn:atom "C"=45 to 55:45 to 55:1 to 10 (for example, Example 25 and so forth), compounds containing copper-zinc and at least one atom "C" selected from the group consisting of magnesium, zirconium, and cerium with the composition ratio thereof being Cu:Zn:atom "C"=45 to 55:45 to 55:1 to 5 (for example, Example 12 and so forth), and compounds containing copper-zinc-barium and at least one atom "C" selected from the group consisting of manganese and lanthanum with the composition ratio thereof being Cu:Zn:Ba:atom "C"=35 to 50:35 to 50:1 to 20:1 to 10 (Example 21 and so forth) are useful not only for the reaction of the present invention to produce an alcohol or a diol compounds by using hydrogen, but also similarly as the catalyst for hydrogenation reactions including a method for producing an alcohol or a diol compound from an ester compound by using hydrogen.

INDUSTRIAL APPLICABILITY

The present invention relates to a method for producing an objective alkanediol having the hydroxy groups at the both molecular terminals thereof such as 1,5-pentanediol with a high reaction selectivity thereto by using a copper-containing metal catalyst which is industrially inexpensive with a convenient procedure.

Among alkanediols having the hydroxy groups at the both molecular terminals thereof produced by the method of the present invention, especially 1,5-pentanediol is useful as a raw material (monomer) for polymers such as, for example, a polyester, a polycarbonate, and a polyurethane, and as a raw material for a pharmaceutical drug and an agricultural chemical, an additive for a resin, a cleaning solvent, and the like.

The invention claimed is:

1. A method for producing an alkanediol having hydroxy groups at both molecular terminals according to formula (2), the method comprising:

contacting a cyclic ether group-comprising methanol having formula (1) with hydrogen in the presence of a metal catalyst;
wherein the metal catalyst comprises a copper atom and at least one co-existing atom selected from the group consisting of elements of the third to the sixth periods of the II to XIV groups (excluding chromium) in the periodical table and lanthanide elements;
wherein formula (1) is:

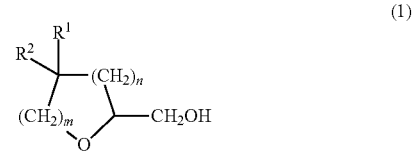

(1)

wherein $R^1$ and $R^2$ are each independently a hydrogen atom, a fluorine atom, a methyl group, or an ethyl group; "n" and "m" each independently are the number of methylene groups; "n" represents an integer of 0, 1, or 2; "m" represents an integer of 1 or 2; and "n+m" is 2 to 4;
wherein formula (2) is:

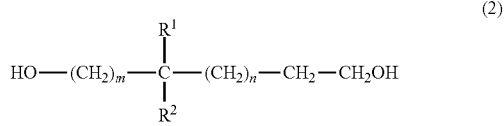

(2)

wherein $R^1$ and $R^2$ are each independently a hydrogen atom, a fluorine atom, a methyl group, or an ethyl group; "n" and "m" each independently are the number of methylene groups; "n" represents an integer of 0, 1, or 2; and "m" represents an integer of 1 or 2.

2. The method of claim 1, wherein the co-existing atom comprises at least one atom "B" selected from the group consisting of zinc, iron, aluminum, and silicon.

3. The method of claim 2, wherein the atom "B" is a zinc atom.

4. The method of claim 2, wherein a mass ratio of the copper atom to the atom "B" is in the range of 10/90 to 99/1.

5. The method of claim 2, wherein the co-existing atom further comprises at least one atom "C" selected from the group consisting of barium, calcium, manganese, lanthanum, cerium, and magnesium.

6. The method of claim 5, wherein a mass ratio of the sum of the copper atom and the atom "B" to the atom "C" is in the range of 10/90 to 99/1.

7. The method of claim 1, wherein the metal catalyst is present in an amount relative to the cyclic ether group-comprising methanol in the range of 0.03 to 10% by mass.

8. The method of claim 1, wherein the cyclic ether group-comprising methanol is tetrahydrofurfuryl alcohol and the alkanediol is 1,5-pentanediol.

9. The method of claim 8, wherein the tetrahydrofurfuryl alcohol is tetrahydrofurfuryl alcohol synthesized using furfural as a raw material.

* * * * *